United States Patent
Holzer

(10) Patent No.: US 12,390,494 B2
(45) Date of Patent: Aug. 19, 2025

(54) COMPOSITIONS AND METHODS FOR TREATING HEART DISEASE

(71) Applicant: Asher Holzer, R'anana (IL)

(72) Inventor: Asher Holzer, R'anana (IL)

(*) Notice: Subject to any disclaimer, the term of this patent is extended or adjusted under 35 U.S.C. 154(b) by 1069 days.

(21) Appl. No.: 17/205,597

(22) Filed: Mar. 18, 2021

(65) Prior Publication Data
US 2021/0275598 A1    Sep. 9, 2021

Related U.S. Application Data

(63) Continuation-in-part of application No. 16/315,195, filed as application No. PCT/IL2017/050745 on Jul. 4, 2017, now abandoned.

Foreign Application Priority Data

Jul. 5, 2016 (IL) .......................... 246608

(51) Int. Cl.
| | | |
|---|---|---|
| A61K 35/545 | (2015.01) | |
| A61K 9/00 | (2006.01) | |
| A61K 9/06 | (2006.01) | |
| A61K 35/28 | (2015.01) | |
| A61K 35/34 | (2015.01) | |
| A61K 47/34 | (2017.01) | |
| A61K 47/38 | (2006.01) | |
| A61M 25/10 | (2013.01) | |
| A61P 9/10 | (2006.01) | |

(52) U.S. Cl.
CPC .......... *A61K 35/545* (2013.01); *A61K 9/0024* (2013.01); *A61K 9/06* (2013.01); *A61K 35/28* (2013.01); *A61K 35/34* (2013.01); *A61K 47/34* (2013.01); *A61K 47/38* (2013.01); *A61M 25/10* (2013.01); *A61P 9/10* (2018.01); *A61M 2025/105* (2013.01); *A61M 2230/04* (2013.01)

(58) Field of Classification Search
CPC ...... A61K 35/28; A61K 35/545; A61K 47/38; A61K 47/34; A61K 9/0024; A61K 35/34; A61K 9/06; A61P 9/10; A61M 25/10; A61M 2025/105; A61M 2230/04
See application file for complete search history.

(56) References Cited

U.S. PATENT DOCUMENTS

| | | |
|---|---|---|
| 5,323,781 A | 6/1994 | Ideker |
| 6,546,270 B1 | 4/2003 | Goldin |
| 8,079,982 B1 | 12/2011 | Ponzi |
| 8,287,532 B2 | 10/2012 | Carroll |
| 8,361,490 B2 | 1/2013 | Holzer |
| 8,709,802 B2 | 4/2014 | Porat |
| 8,936,566 B2 | 1/2015 | Holzer |
| 9,011,411 B2 | 4/2015 | Holzer |
| 9,040,074 B2 | 5/2015 | Holzer |
| 2010/0274129 A1 | 10/2010 | Hooven |
| 2013/0046275 A1 | 2/2013 | Holzer |
| 2014/0335195 A1 | 11/2014 | Houze |

FOREIGN PATENT DOCUMENTS

| | | |
|---|---|---|
| EP | 2525777 B1 | 5/2019 |
| WO | 2006014067 A1 | 2/2006 |
| WO | 2011089604 A2 | 7/2011 |
| WO | 2013011503 A1 | 1/2013 |
| WO | 2013011504 A1 | 1/2013 |
| WO | 2015189586 A1 | 12/2015 |

OTHER PUBLICATIONS

Borden, Bradley Alan; "Transfected mesenchymal stem cells in a thermoreversible hydrogel matrix for the treatment of myocardial infarction"; A dissertation submitted to the faculty of The University of Utah in partial fulfillment of the requirements for the degree of Doctor of Philosophy. Department of Bioengineering, The University of Utah, USA; Aug. 2012 (Aug. 20, 2012); 165 pages.

Committee for Proprietary Medicinal Products (CPMP). Note for Guidance on Non-Clinical Local Tolerance Testing of Medicinal Products. The European Agency for the Evaluation of Medical Products; Evaluation of Medicines for Human Use. Retrieved from: ema.europa.eu/docs/en_GB/document_library/Scientific_guideline /2009/09/ WC500003315.pdf. London, Mar. 1, 2001; CPMP/SWP/ 2145/00; 7 pages.

Escobar-Chávez et al., (2006) Applications of thermo-reversible pluronic F-127 gels in pharmaceutical formulations. J Pharm Pharm Sci 9(3): 339-358.

Freed et al., (2009) Advanced material strategies for tissue engineering scaffolds. Adv Mater 21(32-33): 3410-3418.

Halfon et al., (2011) Markers distinguishing mesenchymal stem cells from fibroblasts are downregulated with passaging. Stem Cells Dev 20(1): 53-66.

Hasan et al., (2015) Injectable Hydrogels for Cardiac Tissue Repair after Myocardial Infarction. Adv Sci (Weinh) 2(11): 1500122; 18 pages.

Kolk et al., (2009) LAD-ligation: a murine model of myocardial infarction. J Vis Exp (32) pii: 1438; 3 pages.

Krishna et al., (2011) Myocardial infarction and stem cells. J Pharm Bioallied Sci 3(2): 182-188.

Ladage et al., (2011) Delivery of gelfoam-enabled cells and vectors into the pericardial space using a percutaneous approach in a porcine model. Gene Ther 18(10): 979-985.

Lin et al., (2013) Commonly used mesenchymal stem cell markers and tracking labels: Limitations and challenges. Histol Histopathol 28(9): 1109-1116.

(Continued)

*Primary Examiner* — Sean C. Barron
(74) *Attorney, Agent, or Firm* — Dorsey & Whitney LLP

(57) ABSTRACT

The present invention provides methods and compositions for treating damage to the heart tissue. In particular, the present invention provides pharmaceutical compositions comprising stem cells embedded in biocompatible thermoreversible hydrogels and use thereof in treating myocardium infarction.

18 Claims, No Drawings

(56) References Cited

OTHER PUBLICATIONS

Liu et al., (2009) Trafficking and differentiation of mesenchymal stem cells. J Cell Biochem 106(6): 984-991.

MacCord Kate (2012) Mesenchyme. The Embryo Project Encyclopedia. Retrieved from: https://embryo.asu.edu/pages/mesenchyme. 8 pages reprint.

Mathieu et al., (2012) Intramyocardial delivery of mesenchymal stem cell-seeded hydrogel preserves cardiac function and attenuates ventricular remodeling after myocardial infarction. PLoS One 7(12): e51991; 12 pages.

Matthew et al., (2002) Effect of mammalian cell culture medium on the gelation properties of Pluronic F127. Biomaterials 23(23): 4615-4619.

Sági et al., (2012) Positional identity of murine mesenchymal stem cells resident in different organs is determined in the postsegmentation mesoderm. Stem Cells Dev 21(5): 814-828.

Sánchez et al., (2013) Use of stem cells in heart failure treatment: where we stand and where we are going. Methodist Debakey Cardiovasc J 9(4): 195-200.

Sheng et al., (2013) Current stem cell delivery methods for myocardial repair. Biomed Res Int 2013: 547902; 16 pages.

Zaim et al., (2012) Donor age and long-term culture affect differentiation and proliferation of human bone marrow mesenchymal stem cells. Ann Hematol 91(8): 1175-118.

COMPOSITIONS AND METHODS FOR TREATING HEART DISEASE

FIELD OF THE INVENTION

The present invention relates to compositions and methods for treating cardiac diseases or disorders. In particular, the present invention relates to pharmaceutical compositions comprising stem cells embedded in biodegradable thermoreversible hydrogels, and use thereof in treating damage due to myocardial infarction.

BACKGROUND OF THE INVENTION

Permanent loss of cardiomyocytes and scar tissue formation after myocardial infarction (MI) results in an irreversible damage to the cardiac function. Cardiac repair by replacement, restoration, and/or regeneration is, therefore, essential to restore function of the heart following MI. So far, the only definitive treatment for heart failure is heart transplantation, which is precluded from wider application due to the limited availability of donor hearts and complications from immunosuppressive therapies. Therefore, there is a great clinical interest to pursue novel treatments for improving heart repair and restoration of function.

The cardiac tissue regeneration with the application of stem cells may be an effective therapeutic option. To date, there are several clinical studies that have demonstrated the potential of stem cell-based therapy in the treatment of MI. These clinical studies have demonstrated a good safety profile, improved cardiac function, and favorable effects in patients with MI (Ananda Krishna et al., J Pharm Bioallied Sci. 2011 April-June; 3(2): 182-188). However, despite the progress in research of stem cell-based cardiac repair, many challenges still remain, such as validating the efficacy and devising robust delivery methods.

Cell types currently investigated for cellular therapy include, inter alia, embryonic stem cells (ESCs), induced pluripotent stem cells (iPSCs), and adult stem cell lineages such as skeletal myoblasts, bone marrow derived stem cells (BMSCs), mesenchymal stem cells (MSCs), and cardiac stem cells (CSCs) (Sheng et al., BioMed Research International 2013 (volume 2013), Article ID 547902).

Along with investigating the proper cells, biomolecules, and drugs to promote cardiac repair and regeneration, the optimal delivery pathway must also be established. A variety of administration routes are currently adopted in clinical studies including direct surgical intramyocardial (IM) injection, catheter-based intramyocardial (IM) administration, transcoronary venous injection, intravenous (IV) infusion and engineered monolayer tissue transplantation (Sheng et al., ibid).

In recent years, injectable hydrogels have been developed and many of them have been proposed for acellular therapies, as drug delivery systems and a support vector for cell delivery and in-vitro cardiac tissue engineering (Hasan et al., Advanced Science, 2015, Volume 2, Issue 11).

Such types of biomaterials are considered to provide an extra cellular matrix (ECM)-like chemical and biophysical environment that offers a proper support for improving the retention, survival, and function of transplanted and recruited cardiogenic cells.

Indeed, a 3D gel may represent an advanced culture system for in vitro cell expansion and the induction of cardiogenic differentiation, wherein cardiogenic differentiation of stem cells can occur through the occurrence of biochemical, topographic and physical cues. Many polymers and other composition such as collagen, fibrin, alginate and PEG and peptides have been evaluated for their ability to form hydrogels in cardiac cell therapy/tissue engineering.

While hydrogels provide new possibilities for a variety of applications including controlled stem cell differentiation in vitro or therapeutic in vivo procedures such as drug and cell delivery or entrapment, their success in cardiac tissue engineering has been limited due to associated weak mechanical properties to allow such architecture to withstand beating environment in vivo and possible complete wash due to exposure to body fluids (Freed, L. E.; et al. Adv. Mater. 2009, 21, 3410-3418).

Materials and gels based on poly(ethylene oxide)-poly(propylene oxide)-poly(ethylene oxide) triblock copolymers (PEO-PPO-PEO) have been studied for pharmaceutical and biomedical applications. These polymers, which are often referred to by the trade name Pluronics® or the generic name poloxamers, are water soluble and exhibit low toxicity, and certain molecular weights have been approved by the FDA for use in the human body, among them Pluronic® F127 ($EO_{100}$-$PO_{65}$$EO_{100}$). It has been shown that the presence of mammalian cell culture medium affects the gelling parameters of Pluronic® F127 (Matthew et al., Biomaterials 23 (2002) 4615-4619). Therefore, the use of hydrogels as a supportive scaffold for living cells remains challenging.

U.S. Pat. No. 9,040,074 discloses a hydrophilic biocompatible sustained-release material comprising Pluronic F-127, PEG-400 and hydroxypropylmethylcellulose (HPMC). The material has low viscosity at room temperature and much higher viscosity at body temperature and will stably adhere to the internal surface of a body cavity.

U.S. Pat. No. 8,936,566 discloses a system for delivering a hydrogel based biocompatible matrix to an internal cavity, the system comprises a delivery device, at least one balloon, and a movable external channel that is adapted to accommodate biocompatible matrix.

U.S. Pat. No. 8,079,982 discloses an injection catheter for infusing therapeutic and diagnostic agents into the heart. The injection catheter comprises a catheter body comprising flexible tubing having proximal and distal ends and at least one lumen therethrough. The catheter further comprises an electrode lead wire having a first end electrically connected to the injection needle and a second end electrically connected to a suitable monitoring apparatus or to a source of ablation energy. The injection needle can thus be used for mapping or ablation in addition to introducing therapeutic and diagnostic agents into the heart.

U.S. Pat. No. 6,546,270 discloses a system for detecting electrode-tissue contact comprising a multi-electrode catheter having a location sensor and a plurality of contact electrodes. The system is suited for use in conjunction with intracardiac electrophysiology or in conjunction with therapeutic procedures such as cardiac ablation.

There is an unmet need for compositions and methods for delivering therapeutic stem cells specifically to the vicinity of a damaged cardiac tissue. It would be highly beneficial to have cells embedded in hydrogels that attach to the damaged tissue, said hydrogels serving as a supporting scaffold for maintaining viable cells for prolonged periods of time.

SUMMARY OF THE INVENTION

The present invention is directed to compositions and methods for applying cells and therapeutic substances to damaged cardiac tissues. The present invention in some embodiments provides pharmaceutical compositions comprising stem cells and/or progenitor cells embedded in biodegradable thermoreversible hydrogels. The present invention in some embodiments further provides methods for treating cardiac tissue by administering stem cells embedded in said hydrogels beneath the pericardium. In particular, the present invention is advantageous in that the compositions comprising cells within the hydrogel are not injected into the cardiac muscle but rather are placed adjacent to the site of damage. In particular, the methods disclosed herein are useful for administering stem cells to the pericardium and for generating a sustainable adherent or viscous scaffold made of a biocompatible hydrogel that maintains the cells at or adjacent to the scar site in need of repair. In some embodiments, the methods disclosed herein are useful for administering stem cells to the proximity of the ganglia for potential treatment of arrhythmia like atrial fibrillation (AFib). The hydrogels described herein provide a vehicle for stem cells that can beneficially deliver the stem cells to the site in a subject that requires treatment without damage to the cells or the tissue to be treated.

It is now disclosed, unexpectedly, that administering stem cells embedded in the biodegradable thermoreversible hydrogel described herein beneath the pericardium exhibits a prolonged and significant therapeutic effect. The present invention is based in part on the unexpected discovery that the biocompatible hydrogel of the invention is sufficiently elastic, having the ability to retain its position and sustain the cells during the periodic contraction and relaxation of the heart muscle. It is further disclosed that the cell-laden thermoreversible hydrogel described herein adheres to the scar surface beneath the pericardium, exhibiting a therapeutic effect, while maintaining the cells viable for long periods of time. The degradation rate of the hydrogels within the body controls the duration of the presence of the cells at the site of damage. The present invention in some embodiments further provides methods for topical treatment of damaged heart muscle in a controlled and predefined period of time. The release of the active material can be controlled through the adjustment of the bio absorbability, biodegradation rate and by controlling the diffusion rate of the different active material within the patch placed on the tissue. The diffusion rate can be controlled by using different patch thickness, porosity of the gel and by using couple of different layers with different diffusion coefficients. This application discloses the supplying of both the cells and factors and other supportive materials through a period of time for the treatment and for the healing of the treated tissue. As described above the existing ways of injection to the heart cardiac muscle or into the coronaries cannot guarantee and cannot control the amount and the duration the cells and the other supportive materials stay at the proximity of the treated tissue. They spread systemically through the body in different rates thus can provide a much lower treatment efficacy. The biocompatible hydrogel of the invention is sufficiently smooth in order to keep the physical property and the amount of adhesion, slickness and other mechanical properties needed for placing a film between the heart and its cover sac. The gel patch has the ability to retain its position and sustain the stem cells and supportive elements (e.g. growth factors) that are needed for the stem cell to flourish and function.

Advantageously, the compositions of the invention maintain the cells at the desired localization while preventing uncontrolled spreading of stem cells that may cause adverse effects. The present invention enables to control the duration of an effective amount of therapeutic cells and other supportive elements in the target area. The elution rate and the treatment time are controlled both through the degradation rate of the gel and by the diffusion from the gel patch into the tissue.

The cardiac muscle fibers undergo constant contraction-relaxation movement. In contrast to administering therapeutic agents to other body internal cavities, the use of the hydrogel for administering cells to the cavity between the myocardia and the pericardium necessitates additional precaution in designing and applying the hydrogel. On the one hand, the hydrogel should be adhesive enough to be retained at the scar site, and on the other hand, it should not damage the lateral movement between the cardiac muscle and the pericardia. The present invention provides two ways to address the challenge: (1) providing a hydrogel with viscosity and adhesiveness that allow it to stick to the injected site, while allowing the contraction-relaxation movement; and (2) applying 2 different layers of the gel having different mechanical properties, in which the layer close to the cardiac muscle is stickier than the layer close to the pericardia, enabling its natural movement.

According to one aspect, the present invention provides a pharmaceutical composition comprising stem cells and/or progenitor cells embedded in biodegradable thermoreversible hydrogel, the hydrogel characterized by a viscosity of less than 200 Pa·s between 4° C. and 12° C., and a viscosity of more than 1,000 Pa·s at 37° C.

According to some embodiments, the hydrogel comprises ethylene oxide/propylene oxide block copolymer and hydroxypropylmethylcellulose (HPMC).

According to an additional aspect, the present invention provides a pharmaceutical composition comprising stem cells and/or progenitor cells embedded in a biodegradable thermoreversible biocompatible hydrogel, wherein the hydrogel comprises ethylene oxide/propylene oxide block copolymer and hydroxypropylmethylcellulose (HPMC). According to some embodiments, the hydrogel is characterized by a viscosity of less than 200 Pa·s between 4° C. and 12° C., and a viscosity of more than 1,000 Pa·s at 37° C.

According to some embodiments, the stem cells are multipotent stem cells. According to other embodiments, the stem cells are adult stem cells. According to some embodiments, the cells are selected from the group consisting of embryonic stem cells (ESCs), induced pluripotent stem cells (iPSCs), myoblasts, bone marrow stem cells (BMSCs), mesenchymal stem cells, cardiac stem cells, and any combination thereof. Each possibility represents a separate embodiment of the invention. According to specific embodiments, the cells are mesenchymal stem cells. According to certain embodiments, the progenitor cells are of the mesodermal lineage. According to some embodiments, the stem cells are not embryonic stem cells.

According to some embodiments, the composition further comprises antigen presenting cells (APC). According to specific embodiments, the APC are dendritic cells. According to some embodiments, the composition comprises multipotent adult stem/pro genitor cells (MASPC) or a population of cells containing MASPC.

According to some embodiments, the composition comprising lineage specific precursor/progenitor (LSP) cells. According to certain embodiments, the LSP cells comprising cells expressing CD304, CD34, CD184, CD309, CD202b, CD3, VEGFR1, and/or any combination thereof. Each possibility represents a separate embodiment of the invention. According to specific embodiments, the cells express CD304. According to other embodiments, the cells express CD34 and CD184. According to other embodiments, the cells express CD309 and CD202b. According to other embodiments, the cells express CD31 and VEGFR1.

According to some embodiments, the cells are homogeneously distributed within the hydrogel. According to alternative embodiments the cells are distributed preferentially within the hydrogel.

According to some embodiments, the hydrogel is characterized by peel strength adhesiveness according to ASTM standard D2256-03 of 0.5-5.0 N cm$^{-2}$ at 37° C. According to certain embodiments, the hydrogel is characterized by peel strength adhesiveness according to ASTM standard D2256-03 of 1.0-5.0 N cm$^{-2}$ at 37° C.

According to some embodiments, the hydrogel is characterized by peel strength adhesiveness according to ASTM standard D2256-03 which is different between its two sides. According to these embodiments, the side towards the heart tissue has a strong adhesion, while the outer side has a minimum adhesion allowing the patch to slide relatively to the heart sac. This may be achieved by applying 2 different layers having different mechanical properties and/or different diffusion coefficients. In addition, the different diffusion coefficient allows the cells to migrate mainly to one direction towards the heart tissue.

According to some embodiments, the hydrogel is characterized by a viscosity of less than 5 Pa·s between 4° C. and 12° C. According to certain embodiments, the hydrogel is characterized by a viscosity of less than 2.5 Pa·s between 4° C. and 12° C. According to certain embodiments, the hydrogel is characterized by a viscosity of less than 0.5 Pa·s between 4° C. and 12° C.

According to some embodiments, the hydrogel is characterized by a peak detachment force of at least 1.3 N. According to certain embodiments, the hydrogel is characterized by a peak detachment force of at least 6.3 N. According to additional embodiments, the hydrogel is characterized by a peak detachment force of at least 14.4 N.

According to some embodiments, the hydrogel is characterized by a peak detachment force of at least 1.3 N. of its one side towards the heart and less than 0.1 N on its outer side towards the heart sac. According to some embodiments, the hydrogel is characterized by a peak detachment force of at least 0.001 N.

According to some embodiments, the hydrogel is characterized by a viscosity of more than $3 \times 10^3$ Pa·s at 37° C.

According to some embodiments, the hydrogel is characterized by a viscosity similar to a typical sun lotion or face cream.

According to some embodiments, the hydrogel is characterized by a viscosity depended on a sheering stress on it. According to some embodiments, the hydrogel comprises between 15% and 35% (w/w) ethylene oxide/propylene oxide block copolymer. According to additional embodiments, the hydrogel comprises between 20% and 30% (w/w) ethylene oxide/propylene oxide block copolymer.

According to some embodiments, the ethylene oxide/propylene oxide block copolymer is a triblock copolymer characterized by an average molecular weight of 13,000 Da and a general formula E106 P70 E106.

According to some embodiments, the hydrogel comprises between 0.01% and 1% (w/w) hydroxypropylmethylcellulose (HPMC). According to certain embodiments, the hydrogel comprises between 0.05% and 0.5% (w/w) hydroxypropylmethylcellulose (HPMC).

According to some embodiments, the hydrogel further comprises polyethylene glycol (PEG).

According to certain embodiments, the hydrogel comprises between 20% and 30% (w/w) ethylene oxide/propylene oxide block copolymer; between 0.05% and 0.5% (w/w) hydroxypropylmethylcellulose (HPMC); between 0.1% and 2.5% (w/w) polyethylene glycol (PEG)-400; in addition to nutrients and isotonicity agents required for sustaining cell viability and the balance water.

According to other embodiments, the hydrogel comprises between 20% and 30% (w/w) ethylene oxide/propylene oxide block copolymer; between 0.1% and 0.3% (w/w) HPMC; between 0.1% and 1.8% (w/w) PEG-400; in addition to nutrients and isotonicity agents required for sustaining cell viability and the balance water.

According to some embodiments, the hydrogel comprises carboxymethyl cellulose (CMC).

According to other embodiments, the hydrogel comprises between 18% and 40% (w/w) ethylene oxide/propylene oxide block copolymer; between 0.05% and 0.8% (w/w) carboxymethyl cellulose (CMC); between 0.1% and 2.5% (w/w) PEG-400; in addition to nutrients and isotonicity agents required for sustaining cell viability and the balance water.

According to some embodiments, the hydrogel comprises between 20% and 30% (w/w) of an ethylene oxide/propylene oxide triblock copolymer characterized by an average molecular weight of 13,000 Da and a general formula E106 P70 E106; between 0.05% and 0.3% HPMC; between 0.4% and 2.5% PEG-400; in addition to nutrients and isotonicity agents required for sustaining cell viability and the balance water.

According to certain embodiments, the hydrogel comprises between 12% and 30% Pluronic F127; between 5% and 30% Pluronic F68; between 0.05% and 2% (w/w) CMC; between 0.1% and 2.5% (w/w) PEG-400; in addition to nutrients and isotonicity agents required for sustaining cell viability and the balance water.

According to some embodiments, the pharmaceutical composition further comprises agents that support the growth and survival of the cells.

According to some embodiments, the pharmaceutical composition further comprises a therapeutic agent suitable for treating heart scar tissue.

According to some embodiments, the hydrogel further comprises a component which is pharmaceutically acceptable and non-toxic to cells selected from the group consisting of adhesive and thickening compounds; bonding agents; pH-modifying substances; diffusion coatings; plasticizers; components for increasing permeability within the hydrogel; swellable excipients; matrix forming polymers; tight junction modifiers/cell membrane permeability enhancers; and any combination thereof.

According to some embodiments, the hydrogel is characterized by releasing said cells, over a temperature range of 36° C.-42° C., and a pH range of between 6.0 and 8.0, at a rate of 80% in a time range of between 3 and 30 hours. According to certain embodiments, the hydrogel is characterized by releasing said cells, over a temperature range of 36° C.-42° C. and a pH range of between 6.5 and 7.5, at a rate of 80% in a time range of between 3 and 30 hours.

According to other embodiments, the hydrogel is characterized by releasing said cells, over a temperature range of 36° C.-42° C. and a pH range of between 6.0 and 8.0, at a rate of 80% in a time range of between 2 and 4 days.

According to some embodiments, the hydrogel is characterized by releasing said cells, over a temperature range of 36° C.-42° C. and a pH range of between 6.0-8.0, at a rate of 80% in a time range of between 2 and 4 weeks.

According to some embodiments, the pharmaceutical composition further comprises supporting material for the cells.

According to some embodiments, the pharmaceutical composition further comprises an agent selected from the group consisting of antineoplastic agents, anti-infective agents, antimicrobial agents, antiparasitic agents, antiviral agents, agents acting on the blood, antihemorrhagics, antithrombotic agents, antifungals, antiseptics, anti-inflammatory agents, gene therapy agents, corticosteroids, analgesic and anesthetic agents, growth factors, VEGF, inhibitory factors, proteins, mucin, and any combination thereof.

According to some embodiments, the hydrogel is characterized by flexibility sufficient to permit the volume of the tissue to which said composition is applied to expand by a factor of at least 3 without detachment of said gel from said tissue.

According to some embodiments, the hydrogel is characterized by flexibility sufficient to allow the tissue to which said composition is applied to, to move, contract, and/or expand with no significant loss of its original flexibility.

According to some embodiments, the pharmaceutical composition according to the present invention is for use in treating a cardiac disease or disorder.

According to some embodiments, the pharmaceutical composition according to the present invention is for use in treating myocardial infarction.

According to some embodiments, the pharmaceutical composition according to the present invention is for use in treating the ganglia in order to treat myocardial tachycardia or arrhythmia.

According to some embodiments, the pharmaceutical composition according to the present invention is for use in treating myocardial tachycardia or arrhythmia.

According to some embodiments, the pharmaceutical composition is administered beneath the pericardium of a subject in need thereof. According to certain embodiments, the treating comprises administering the pharmaceutical composition beneath or above the pericardium and adjacent to the scar tissue.

According to certain embodiments, the treating comprises administering the pharmaceutical composition beneath the parietal layer and above the pericardium and adjacent to the scar tissue.

According to some embodiments, the hydrogel can be placed between the parietal layer and the epicardium (visceral) layer having strong adhesion to the epicardium and smooth non-adhesive side towards the parietal layer or vice versa.

According to some embodiments, the hydrogel can be placed in any cleavage plan to be created.

According to an additional aspect, the present invention provides a method for treating a cardiac disease or disorder in a subject in need thereof, the method comprising administering between the parietal layer and the epicardium layer of said subject a pharmaceutical composition comprising stem cells and/or progenitor cells embedded in a biodegradable thermoreversible hydrogel, wherein the hydrogel is characterized by a viscosity of less than 200 Pa·s between 4° C. and 12° C., and a viscosity of more than 1,000 Pa·s at 37° C., and/or wherein said hydrogel comprises ethylene oxide/propylene oxide block copolymer, hydroxypropylmethylcellulose (HPMC) and an adhesive agent.

According to some embodiments, the method comprises a step of applying 2 different layers having different mechanical properties and/or different diffusion coefficients. According to certain embodiments, the method comprises applying the second layer immediately after the first one. According to certain embodiments, the method comprises applying the second layer at least 1 min after applying the first one. According to additional embodiments, the method comprises applying the second layer 5 min to 1 hour after applying the first one. According to other embodiments, only the layer that close to the cardiac muscle comprising cells.

According to some embodiments, the method comprises a step of applying 2 different layers having different adhesion properties.

According to some embodiments, the method comprises a step of applying 2 different layers having different degradation rate.

According to some embodiments, the method comprises a step of applying 2 different layers having different active therapeutic agents.

According to another aspect, the present invention provides a method for treating cardiac disease in a subject in need thereof, the method comprises administering beneath the pericardium or beneath the parietal layer of said subject a pharmaceutical composition comprising cells embedded in a biodegradable thermoreversible hydrogel according to the present invention.

According to an additional aspect, the present invention provides a method for accurate delivery of a pharmaceutical composition according to the present invention to a precise location beneath the pericardium for a controlled duration without penetrating the cardiac muscle, the method comprising:
(i) mixing a therapeutically effective amount of stem cells and/or progenitor cells and the biodegradable thermoreversible hydrogel of the invention;
(ii) inflating a balloon to open a cavity between the myocardium and the pericardium, and adjacent to the presumptive scar tissue localization;
(iii) identifying the heart scar tissue localization; and
(iv) releasing the mixture of step (i) into the scar tissue localization identified in step (iii).

According to some embodiments, step (iii) comprising detecting ECG signal levels for identifying the heart scar tissue localization.

According to other embodiments, the scar tissue localization is detected by CT, MRI, or US.

DETAILED DESCRIPTION OF THE INVENTION

The present invention provides stem cells and/or progenitor cells embedded in biocompatible thermoreversible hydrogels and use thereof for treating cardiac diseases. In addition, methods of treating cardiac tissue that comprise the step of administering beneath the pericardium stem cells embedded in said hydrogel are provided.

The methods of the present invention are advantageous over previously known methods for administering cell-laden hydrogels to the cavity beneath the pericardium. The hydrogels described herein stick to the scar tissue and provide a supportive scaffold to the cells. The hydrogels described herein maintain the cells viability for prolonged periods of time, thereby preventing the spreading of the cells in the body, and thereby the potential adverse effects. The methods described herein may reduce the required amount of cells per treatment as well as the number of treatments. Moreover, since stem cells production is highly expensive, it is highly advantageous to locate them at the target site, which increases therapeutic efficiency.

The hydrogels described herein maintain the cells at the scar vicinity and enable a prolonged interaction between the stem cells and the targeted tissue. The movement/diffusion of the administered cells depends on the cells concentration and can be manipulated as required. The elution rate of the cells can be controlled through the gel porosity and diffusion coefficients of the gel as well as through the degradation rate of the gel. In addition, the cell concentration at the damaged tissue is tightly controlled. The pharmaceutical compositions of the invention may further contain compounds that support cell viability.

The hydrogels described herein maintain the physical properties among the different layers of the heart sac. A special care is required to avoid the different layers to stick to each other, which may lead to a restriction in heart range of motion.

The present invention can be advantageously used for treating cardiac diseases and disorders such as myocardial infarction and/or arrhythmia.

According to one aspect, the present invention provides a pharmaceutical composition comprising stem cells and/or progenitor cells embedded in biodegradable thermoreversible hydrogel, the hydrogel characterized by a viscosity of less than 200 Pa·s between 4° C. and 12° C., and a viscosity of more than 1,000 Pa·s at 37° C.

According to an additional aspect, the present invention provides a pharmaceutical composition comprising therapeutic cells embedded in a biodegradable thermoreversible biocompatible hydrogel as described herein. The cells can be any cells that may facilitate a therapeutic activity to a damaged heart. Preferably, the cells are stem cells.

A "hydrogel" is defined as a substance formed when a polymer (natural or synthetic) becomes a 3-D open-lattice structure that entraps solution molecules, typically water, to form a gel. A polymer may form a hydrogel by, for example, aggregation, coagulation, hydrophobic interactions, cross-linking, salt bridges, etc.

The phrase "biodegradable" as used herein refers to the hydrogel which degrade in vivo, and wherein erosion of the hydrogel over time occurs concurrent with or subsequent to release of the embedded cells.

The term "thermoreversible" means that it is convertible from a liquid phase at room temperature to a gel phase at a body temperature. The term "room temperature" refers to an ambient temperature of about 25° C., and it can range from 20° C. to 27° C.; the term "body temperature" refers to a temperature of core body of a human body of 37° C., and it can range from 35° C. to 40° C.

The term "cells embedded in a hydrogel" means that cells are carried by the hydrogel or dispersed within the hydrogel matrix. It is to be understood that the cells may be dispersed homogeneously within the hydrogel or alternatively they may be non-homogeneously dispersed at one or more particular locations within such a matrix, including the surface of the hydrogel.

According to some embodiments, the hydrogel is characterized by peel strength adhesiveness according to ASTM standard D2256-03 of 0.5-5.0 N cm$^{-2}$ at 37° C. According to certain embodiments, the hydrogel is characterized by peel strength adhesiveness according to ASTM standard D2256-03 of 1.0-5.0 N cm$^{-2}$ at 37° C. According to certain embodiments, the hydrogel is characterized by peel strength adhesiveness according to ASTM standard D2256-03 of more than 3 N cm$^{-2}$ at 37° C. According to additional embodiments, the hydrogel is characterized by peel strength adhesiveness according to ASTM standard D2256-03 of more than 1 N cm$^{-2}$ at 37° C.

According to some embodiments, the hydrogel is characterized by a viscosity of less than 5 Pa·s between 4° C. and 12° C. According to certain embodiments, the hydrogel is characterized by a viscosity of less than 2.5 Pa·s between 4° C. and 12° C. According to certain embodiments, the hydrogel is characterized by a viscosity of less than 0.5 Pa·s between 4° C. and 12° C.

According to some embodiment, the hydrogel is characterized by a peak detachment force of at least 1.3 N. According to certain embodiments, the hydrogel is characterized by a peak detachment force of at least 6.3 N. According to additional embodiments, the hydrogel is characterized by a peak detachment force of at least 14.4 N.

The term "peak detachment force" as used herein refers to a method of measuring the force required to detach the hydrogel of the invention from a certain surface.

According to some embodiments, the hydrogel comprises ethylene oxide/propylene oxide block copolymer and hydroxypropylmethylcellulose (HPMC).

According to some embodiments, the hydrogel comprises between 0.01% and 1% (w/w) hydroxypropylmethylcellulose (HPMC). According to certain embodiments, the hydrogel comprises between 0.05% and 0.5% (w/w) hydroxypropylmethylcellulose (HPMC).

According to some embodiments, the hydrogel further comprises polyethylene glycol (PEG). According to some embodiments, the hydrogel comprises PEG-800 or PEG-400.

According to certain embodiments, the hydrogel comprises between 20% and 30% (w/w) ethylene oxide/propylene oxide block copolymer; between 0.05% and 0.5% (w/w) hydroxypropylmethylcellulose (HPMC); between 0.1% and 2.5% (w/w) polyethylene glycol (PEG)-400.

According to other embodiments, the hydrogel comprises between 20% and 30% (w/w) ethylene oxide/propylene oxide block copolymer; between 0.1% and 0.3% (w/w) HPMC; between 0.1% and 1.8% (w/w) PEG-400.

According to other embodiments, the hydrogel comprises between 18% and 40% (w/w) ethylene oxide/propylene oxide block copolymer; between 0.05% and 0.8% (w/w) Carboxymethyl cellulose (CMC); between 0.1% and 2.5% (w/w) PEG-400.

According to some embodiments, the hydrogel comprises between 20% and 30% (w/w) of an ethylene oxide/propylene oxide triblock copolymer characterized by an average molecular weight of 13,000 Da and a general formula E106 P70 E106; between 0.05% and 0.3% HPMC; between 0.4% and 2.5% PEG-400.

According to certain embodiments, the hydrogel comprises between 12% and 30% Pluronic F127; between 5% and 30% Pluronic F68; between 0.05% and 2% (w/w) CMC; between 0.1% and 2.5% (w/w) PEG-400.

Aqueous solutions of poloxamers are stable in the presence of acids, alkalis, and metal ions. Commonly used poloxamers include the 88 (F-68 grade), 237 (F-87 grade), 338 (F-108 grade) and 407 (F-127 grade) types, which are freely soluble in water. The "F" designation refers to the flake form of the product. PF-127 has a good solubilizing capacity, low toxicity and is, therefore, considered a good medium for drug delivery systems.

According to an aspect, the present invention provides a method for treating cardiac disease in a subject in need thereof, the method comprises administering beneath the pericardium a pharmaceutical composition comprising stem cells and/or progenitor cells embedded in a biodegradable thermoreversible biocompatible hydrogel, the hydrogel comprises between 20% and 30% (w/w) of an ethylene oxide/propylene oxide triblock copolymer characterized by an average molecular weight of 13,000 Da and a general formula E106 P70 E106; between 0.05% and 0.3% HPMC; between 0.4% and 2.5% PEG-400; and the balance water.

PF-127 is a commercially available polyoxyethylene-polyoxypropylene triblock copolymer that possesses a general formula E106 P70 E106, with an average molecular mass of 13,000 Da. It contains approximately 70% ethylene oxide, which accounts for its hydrophilicity. It is one of the series of poloxamer ABA block copolymers, whose members share the following chemical formula:

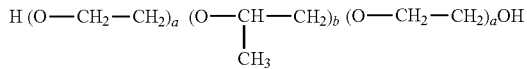

PF-127 aqueous solutions of 20 to 30% w/w posses characteristic of reverse thermal gelation, i.e., they are liquid at refrigerated temperatures (4-5° C.), but gel upon warming to room temperature. The gelation is reversible upon cooling. This phenomenon, therefore, suggests that when injected into a body cavity, the gel preparation will form a solid artificial fabric. PF-127 has been reported to be the least toxic of commercially available copolymers.

PF-127 is more soluble in cold water than in hot water as a result of increased solvation and hydrogen bonding at lower temperatures.

The hydrogel is biocompatible. The biocompatible hydrogel polymer matrix is slowly bioabsorbed, dissolved, and/or excreted. According to some embodiments, the biocompatible hydrogel comprises a bioabsorbable polymer. According to some embodiments, the polymer is bioabsorbed within about 3 to 30 days. According to some embodiments, the polymer is bioabsorbed within about 30 to 180 days. According to some embodiments, the polymer is bioabsorbed within about 1 to 60 days. According to some embodiments, the polymer is bioabsorbed within about 14 to 180 days. According to certain embodiments the polymer is bioabsorbed within about 365 days, 180 days, about 120 days, about 90 days, about 60 days, about 28 days, about 21 days, about 14 days, about 10 days, about 7 days, about 6 days, about 5 days, about 4 days, about 3 days, about 2 days, or about 1 day. According to some embodiments the polymer is bioabsorbed within less than 365 days, less than 180 days, less than 120 days, less than 90 days, less than 60 days, less than 30 days, less than 28 days, less than 21 days, less than 14 days, less than 10 days, less than 7 days, less than 6 days, less than 5 days, less than 4 days, less than 3 days, less than 2 days, or less than 1 day. According to other embodiments the polymer is bioabsorbed within more than 365 days, 180 days, more than 120 days, more than 90 days, more than 60 days, more than 28 days, more than 21 days, more than 14 days, more than 10 days, more than 7 days, more than 6 days, more than 5 days, more than 4 days, more than 3 days, more than 2 days, or more than 1 day. According to additional embodiments, the polymer is bioabsorbed within about 3 to 30 hours. According to certain embodiments, the biocompatible hydrogel polymer matrix is substantially non-bioabsorbable.

The term "bioabsorbable," as used herein, refers to the ability of a tissue-compatible material to degrade in the body after implantation into nontoxic products which are eliminated from the body or metabolized.

According to some embodiments, the concentration of the cells within the pharmaceutical composition according to the invention influences the speed of degradation of the hydrogel.

According to some embodiments, the stem cells are embryonic stem cells. According to other embodiments, the stem cells are adult stem cells. According to some embodiments, the cells are selected from the group consisting of embryonic stem cells (ESCs), induced pluripotent stem cells (iPSCs), myoblasts, bone marrow stem cells (BMSCs), masenchymal stem cells, cardiac stem cells, and any combination thereof. Each possibility represents a separate embodiment of the invention. According to specific embodiments, the cells are masenchymal stem cells. According to certain embodiments, the progenitor cells are of the mesodermal lineage.

The term "stem cells" as used herein refers to cells that have the capacity to self renew (i.e., go through numerous cycles of cell division while maintaining the undifferentiated state) and to differentiate into specialized cell types.

The term "progenitor cells" as used herein and by those skilled in the art means a committed or specialized precursor with proliferative capability.

As used herein, the term "induced pluripotent stem cells" refers to a pluripotent stem cell derived from a somatic cell (e.g. an adult somatic cell). Induced pluripotent stem cells are similar to embryonic stem cells in their differentiation abilities to form any adult cell types, but are not derived from an embryo. Cells may be autologous or taken from a bank line of cells.

Induced pluripotent stem cells (iPSC) may be generated from adult somatic cells by any method, including but not limited to reprogramming to the embryonic state by viral or non-viral based methods. These iPSCs resemble embryonic stem cells in self renewal capacities and differentiation potential to various cell types including cardiomyocytes.

As used herein, the term "pluripotent" refers to the potential of a stem cell to make any differentiated cell type of an organism.

According to some embodiments, the mesenchymal stem cells express one or more of the positive MSC markers CD105, CD144, CD44, CD166, or CD90. According to some embodiments, the mesenchymal stem cells do not express one or more of the negative MSC markers CD34 and CD116. Mesenchymal stem cell markers are described, for example, in Lin et al., Histol. Histopathol. 28:1109-1116 (2013), and in Halfon et al., Stem Cells Dev. 20:53-66 (2011).

As used herein, a "positive" mesenchymal stem cell marker is a marker on the surface of the cell that is unique to mesenchymal stem cells. According to some embodiments, at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or more of the MSC cells are positive for one or more of the CD markers CD105, CD144, CD44, CD166, or CD90.

As used herein, a "negative" mesenchymal stem cell marker is a marker on the surface of the cell that is distinctly not expressed by mesenchymal stem cells. According to some embodiments, a negative mesenchymal stem cell marker is CD34 or CD116. According to some embodiments, at least 25%, at least 30%, at least 35%, at least 40%, at least 45%, at least 50%, at least 55%, at least 60%, at least 65%, at least 70%, at least 75%, or more of the MSC cells are negative for one or more of the CD markers CD34 and CD116.

The presence and/or amount of a marker of interest on a mesenchymal stem cell can be determined according to any method of nucleic acid or protein expression known in the art. Nucleic acid may be detected using routine techniques such as northern analysis, reverse-transcriptase polymerase chain reaction (RT-PCR), microarrays, sequence analysis, or any other methods based on hybridization to a nucleic acid sequence that is complementary to a portion of the marker coding sequence (e.g., slot blot hybridization). Protein may be detected using routine antibody-based techniques, for example, immunoassays such as ELISA, Western blotting, flow cytometry, immunofluorescence, and immunohistochemistry. According to some embodiments, the presence and/or amount of a marker of interest is determined by immunoassay (e.g., ELISA) as described above.

As used herein, the term "mesenchymal stem cell" refers to a multipotent stem cell (i.e., a cell that has the capacity to differentiate into a subset of cell types) that can differentiate into a variety of cell types, including osteoblasts, chondrocytes, and adipocytes. Mesenchymal stem cells can be obtained from a variety of tissues, including but not limited to bone marrow tissue, adipose tissue, muscle tissue, birth tissue (e.g., amnion, amniotic fluid, or umbilical cord tissue), skin tissue, bone tissue, and dental tissue.

MSCs are used in a variety of therapies, such as the treatment of Age-related Macular Degeneration (AMD) and myocardial infarct. Once administered to the patient, the MSCs typically migrate (or home) to the damaged tissue and exert their therapeutic effects through paracrine signaling and by promoting survival, repair and regeneration of the neighboring cells in the damaged tissue.

According to exemplary embodiments, the cells are allogeneic mesenchymal precursor cells (Rexlemestrocel-L).

According to some embodiments, the pharmaceutical composition comprises a population of cells enriched with stem cells and/or progenitor cells. Non-limiting examples of cells that may be used according to the present invention are disclosed in U.S. Pat. No. 8,709,802. For example, APC and/or DC are used to direct activation and/or effect differentiation of tissue-derived cells (TDC). The term TDC means a population containing stem/progenitor cells and other cells such as mature cells, the TDC have been derived from an original population of cells, e.g., peripheral blood mononuclear cells (PBNC), in a tissue by (a) isolating at least a first sub population of the population from a second sub-population of the population, and (b) increasing the proportion of stem/progenitor cells in the first sub-population of cells. In one example, the APC, typically dendritic cells, are used to differentiate TDC population, resulting in a specific population of cells (e.g., lineage specific precursor/progenitors (LSP)). In additional non-limiting example, TDC of enriched MASPC was shown to differentiate into an LSP of endothelial progenitor cells (EPC).

According to some embodiments, the composition further comprises antigen presenting cells (APC). According to specific embodiments, the APC are dendritic cells. According to some embodiments, the composition comprises multipotent adult stem/pro genitor cells (MASPC) or a population of cells containing MASPC.

According to some embodiments, the composition comprising lineage specific precursor/progenitor (LSP) cells. According to certain embodiments, the LSP cells comprising cells expressing CD304, CD34, CD184, CD309, CD202b, CD3, VEGFR1, and/or any combination thereof. Each possibility represents a separate embodiment of the invention. According to specific embodiments, the LSP cells comprising cells expressing CD304. According to other embodiments, the LSP cells comprising cells expressing CD34 and CD184. According to other embodiments, the LSP cells comprising cells expressing CD309 and CD202b. According to other embodiments, the LSP cells comprising cells expressing CD31 and VEGFR1.

According to some embodiments, at least 2.5% of the LSP cell population express one or more markers selected from the group consisting of CD31, CD133, CD144, CD202b, von Willebrand factor (VWF), CD102, CD105, CD106, CD109, CD114, CDw145, CD201, CD299, and CD309. According to other embodiments, at least 2.5% of the LSP cell population express one or more markers selected from the group consisting of CD7, CD31, CD33, CD34, CD90, CD105, CD115, CD117, CDw123, CD124, CD157, CD164, CD172a, CD173. CD175, CD175, CD178, CD184, CD191, CD202b, CD292, and Stro-1.

According to some embodiments, at least 5% of the antigen-presenting cells express one or more markers selected from the group consisting of: CD1c, CD80, CD83, CD86, CD141, CD218, CD301, CD303, and CD304.

According to certain embodiments, the composition comprises an isolated population of at least 5 million lineage specific precursor/progenitor (LSP) cells comprising a first, a second and a third subpopulation of cells, wherein the first subpopulation of cells comprises at least 5.9% of the total LSP cell population and expresses CD304, wherein the second subpopulation of cells comprises at least 2.0% of the total LSP cell population and expresses CD34 and CD184, and wherein the third subpopulation of cells comprises the remainder of the LSP cell population, wherein the third subpopulation of cells comprises a CD309 and CD202b expressing population, and wherein the CD309 and CD202b expressing population comprises at least 0.2% of the total LSP cell population, wherein the third subpopulation of cells further comprises a CD31 and VEGFR1 expressing population, and wherein the CD31 and VEGFR1 expressing population comprises at least 2.3% of the total LSP cell population, and wherein the third subpopulation of cells further comprises a population of cells that uptake Ac-LDL and express Ulex lectin, and wherein the population of cells that uptake Ac-LDL and express Ulex lectin comprises between 7% and 41.5% of the total LSP cell population.

According to additional embodiments, the pharmaceutical composition comprises the MPC-150-IM cells of Mesoblast Ltd.

According to other embodiments, the cells are autologous G-CSF-mobilized peripheral blood-derived CD34.

According to some embodiments, the pharmaceutical composition further comprises a medium including at least one component selected from the group consisting of IL-10, IL-12, IL-18, IL-27, TGF beta, bFGF, and VEGF. Each possibility represents a separate embodiment of the invention.

According to some embodiments, the cells are homogeneously distributed within the hydrogel.

Ischemic tissue environment, oxidative stress, and loss of ECM are the major challenges of cell survival in vivo. In addition, the concentration of cells within the hydrogel and the presence of nutrient factors have a crucial affect on cell viability. In order to increase cell survival, stress preconditioning can be performed.

The term "preconditioning" as used herein refers to exposing the cells to stress before administering to a patient.

According to some embodiments, the cells are preconditioned before mixing with the hydrogel of the invention. According to other embodiments, the cells are preconditioned after mixing the cells with the hydrogel of the invention.

According to some embodiments, the method of treating as described above comprises preconditioning of the cells.

According to certain embodiments, the cells are preconditioned with hypoxia, oxidation, or heat shock.

According to some embodiments, the biocompatible thermoreversible hydrogel described herein provide improved cell viability over cells injected without the use of the hydrogel.

According to some embodiments, the pharmaceutical composition comprises cells at a concentration of between 100 to $1\times10^7$ cells per mL. According to some embodiments, the pharmaceutical composition comprises cells at a concentration of between 100 to $1\times10^6$ cells per mL. According to certain embodiments, the pharmaceutical composition comprises cells at a concentration of between 200 to $5\times10^5$ cells per mL. According to certain embodiments, the pharmaceutical composition comprises cells at a concentration of between 500 to $1\times10^5$ cells per mL. According to certain embodiments, the pharmaceutical composition comprises cells at a concentration of between 500 to $5\times10^4$ cells per mL. According to additional embodiments, the pharmaceutical composition comprises cells at a concentration of between 1000 to $2\times10^4$ cells per mL. According to other embodiments, the pharmaceutical composition comprises cells at a concentration of between 50 to $5\times10^5$ cells per mL.

According to some embodiments, the pharmaceutical composition further comprises agents that support the growth and survival of the cells.

According to some embodiments, the pharmaceutical composition further comprises a therapeutic agent suitable for treating heart scar tissue.

According to some embodiments, the hydrogel further comprises a component which is pharmaceutically acceptable and non-toxic to cells selected from the group consisting of adhesive and thickening compounds; bonding agents; pH-modifying substances; diffusion coatings; plasticizers; components for increasing permeability within the hydrogel; swellable excipients; matrix forming polymers; tight junction modifiers/cell membrane permeability enhancers; and any combination thereof.

According to some embodiment, the bonding agent which is pharmaceutically acceptable and non-toxic to cells is selected from the group consisting of: polycarbophil, cellulose, microcrystalline cellulose, cellulose derivatives, HPMC, hydroxypropylcellulose (HPC), low-substituted hydroxypropylcellulose, dicalcium phosphate, lactose, sucrose, ethylcellulose, hydroxypropymethylcellulose acetate succinate (HPMCAS), polyvinylpyrrolidone (PVP), vinylpyrrolidone/vinyl acetate copolymer, polyethylene glycol, polyethylene oxide, polymethacrylates, polyvinyl alcohols (PVA), partially hydrolyzed polyvinyl acetate (PVAc), polysaccharides, hyaluronic acid, fats, fatty acid derivatives, and any combination thereof.

According to some embodiments, the hydrogel further comprising humectants. According to some embodiments, the humectant is selected from the group consisting of glycerol, propylene glycol and sorbitol.

According to some embodiments, the diffusion coating which is pharmaceutically acceptable and non-toxic to cells is selected from the group consisting of ethylcelluloses, polymethacrylates, cellulose acetate, cellulose acetate butyrate, and any combination thereof.

According to some embodiments, the component for increasing permeability within the hydrogel which is pharmaceutically acceptable and non-toxic to cells is selected from the group consisting of polyethylene glycols, PVP, PVA, HPMC, HPC, hydroxyethylcelluloses (HEC), methylcellulose (MC), carboxymethylcelluloses and their salts, dextrins, maltodextrins, cylcodextrins, dextrans, urea, salts, sugars, sugar alcohols, and any combination thereof.

According to some embodiments, the swellable excipient which is pharmaceutically acceptable and non-toxic to cells is selected from the group consisting of polyvinylpyrrolidones, crospovidones, crosslinked sodium carboxymethylcellulose, crosslinked sodium carboxymethylstarch, polyethylene oxides, polymethyacrylates, low substituted hydroxypropylcellulose (L-HPC), cellulose acetate, ethylcellulose, polymethacrylates, high-molecular weight polyethylene oxides, xanthan gum, copolymers of vinylpyrrolidone and vinyl acetate, poly(hydroxyalkyl methacrylate), alginates, galactomannans, and any combination thereof.

According to some embodiments, the matrix forming polymer which is pharmaceutically acceptable and non-toxic to cells is selected from the group consisting of hydroxyethylmethylcelluloses, hydroxypropylcellulose (HPC), hydroxyethylcellulose (HEC), Methylcellulose (MC), ethylcelluloses, alkylcelluloses, hydroxyalkylcelluloses, hydroxyalkylmethylcelluloses, sodium CMCs, alginates, galactomannans, xanthans, polyethylene oxides, polyacrylic acids, polymethacrylic acids, polymethacrylic acid derivatives, polyvinyl alcohols, partially hydrolyzed polyvinyl acetate, polyvinylpyrrolidone, agar, pectin, gum arabic, tragacanth, gelatin, starch, starch derivatives poly (propylene oxide) (PPO), poly(lactide-co-glycolic acid) (PLGA), poly(N-isopropylacrylamide) (PNIPAM), polypropylene fumarate (PPF), polyurethane (PU), poly(organophosphazene) (POP), stearic acid, poly(acrylic acid), glyceryl stearate, cetearyl alcohol, sodium stearoyl lactylate, hydroxy-lanolin, and any combination thereof.

According to some embodiments, the pH-modifying substances are selected from the group consisting of acids, bases and buffers. According to certain embodiments, the pH-modifying substance is selected from the group consisting of: adipic acid, malic acid, L-arginine, ascorbic acid, aspartic acid, benzenesulphonic acid, benzoic acid, succinic acid, citric acid, ethanesulphonic acid, 2-hydroxyethanesulphonic acid, fumaric acid, gluconic acid, glucuronic acid, glutamic acid, potassium hydrogen tartrate, maleic acid, malonic acid, methanesulphonic acid, toluenesulphonic acid, trometamol, and tartaric acid.

According to some embodiments, the hydrogel is characterized by releasing said cells, over a temperature range of 36° C.-42° C. and a pH range of between 6 and 8.0, at a rate of 80% in a time range of between 3 and 30 hours. According to certain embodiments, the hydrogel is characterized by releasing said cells, over a temperature range of 36° C.-42° C. and a pH range of between 6.5 and 7.5, at a rate of 80% in a time range of between 3 and 30 hours. According to other embodiments, the hydrogel is characterized by releasing said cells, over a temperature range of 36° C.-42° C. and a pH range of between 6 and 8.0, at a rate of 80% in a time range of between 2 and 4 weeks.

The pharmaceutical compositions described herein are designed not to influence the motion, expansion and contraction of the heart muscle and remain attached to the damaged tissue.

According to some embodiments, the hydrogel is characterized by flexibility sufficient to permit the volume of the cardiac tissue to which said composition is applied to expand by a factor of at least 3 without detachment of said gel from said tissue. For example, the hydrogel flexibility is sufficient such that a 3 cm²×3 cm² section of tissue layered with said hydrogel at room temperature can be stretched to 9 cm²×9 cm² without detachment of the hydrogel from said tissue.

According to some embodiments, the hydrogel is additionally used as biological glue.

According to some embodiments, the pharmaceutical composition further comprises an agent selected from the group consisting of antineoplastic agents, chemotherapeutic agents, anti-infective agents, antimicrobial agents, antiparasitic agents, antiviral agents, agents affecting blood, antihemorrhagics, antithrombotic agents, antifungals, antiseptics, anti-inflammatory agents, gene therapy agents, corticosteroids, analgesic and anesthetic agents, growth factors, VEGF, inhibitory factors, proteins, mucin, and any combination thereof.

According to some embodiments, the pharmaceutical composition according to the present invention is for use in treating a cardiac disease or disorder.

The terms "treatment", "treat", "treating", and the like, are meant to include slowing or reversing the progression of a disorder. These terms also include alleviating, ameliorating, attenuating, eliminating, or reducing one or more symptoms of a disorder or condition, even if the disorder or condition is not actually eliminated and even if progression of the disorder or condition is not itself slowed or reversed.

As used herein, the term "cardiac disease or disorder" is a broad concept encompassing all kinds of cardiac diseases and disorders that may benefit from stem cells therapy and may include, for example, myocardial infarction, heart hypertrophy, heart failure, congestive heart failure, angina pectoris, ischemic disorders, tachycardia, various kinds of arrhythmia like atrial fibrillation (AFIB), ventricular tachycardia (VT), Flutter, supraventricular tachycardia (SVT), etc.

According to some embodiments, the pharmaceutical composition according to the present invention is for use in treating myocardial infarction.

As used herein, the term "myocardial infarction" encompasses a singular myocardial infarction or a plurality of myocardial infarctions. According to some embodiments, the infarction results in scar tissue.

According to some embodiments, the treating comprises administering the pharmaceutical composition beneath the pericardium of a subject in need thereof. According to certain embodiments, the treating comprises administering the pharmaceutical composition beneath the pericardium and adjacent to the scar tissue.

The term "beneath the pericardium" as used herein refers to the location between the pericardium and the myocardium or between the parietal layer and the epicardium, or any layer underneath the heart sac.

According to another aspect, the present invention provides a method for treating cardiac disease in a subject in need thereof, the method comprises administering to the pericardium a pharmaceutical composition comprising cells embedded in a biodegradable thermoreversible biocompatible hydrogel according to the invention.

According to some embodiments, the pharmaceutical composition is administered beneath the pericardium.

The pharmaceutical composition of the invention can be administered using any known practice. In some embodiments, an adapted device is used for locating the cells-embedded hydrogel in the scar tissue area. For example, the pharmaceutical composition of the invention may be administered using a catheter apparatus as described in U.S. Pat. Nos. 8,079,982 and 8,936,566.

According to an additional aspect, the present invention provides a method for accurate delivery of a pharmaceutical composition according to the invention to a precise location beneath the pericardium without penetrating the cardiac muscle, the method comprising:
(i) mixing an effecting amount of stem cells and/or progenitor cells into the biodegradable thermoreversible hydrogel of the invention;
(ii) separating the myocardium and the pericardium tissues, thereby generating a cavity between said tissues; and
(iii) releasing the mixture of step (i) into the heart scar tissue localization.

According to some embodiments, the method further comprises a step of detecting ECG signal levels for identifying a scar tissue localization.

According to some embodiments, step (i) further comprises adding of a cell supporting agent.

According to some embodiments, the supporting agent is selected from the group consisting of amino acid, monosaccharide, vitamin, inorganic ion, hormone, pH adjusting agent, growth factor, and any combination thereof. Each possibility represents a separate embodiment of the invention.

According to some embodiments, the separating step is performed by inflating a balloon.

In a non-limiting example, the cavity beneath the pericardium can be separated by an apparatus described in US Application Publication No. 20100274129.

According to an additional aspect, the present invention provides a method of treating a cardiac disease or disorder in a subject in need thereof, the method comprising administering beneath the pericardium a hydrogel as described herein and an effective amount of a therapeutic agent.

According to some embodiments, the therapeutic agent is selected from the group consisting of anti-infective agents, antimicrobial agents, antiparasitic agents, antiviral agents, agents acting on the blood, antihemorrhagics, antithrombotic agents, antifungals, antiseptics, anti-inflammatory agents, neurological agents, gene therapy agents, corticosteroids, analgesic and anesthetic agents, growth factors, VEGF, inhibitory factors, LIF, proteins, mucin, blood vessels growth enhancers, and any combination thereof.

According to some embodiments, the growth factor is selected from the group consisting of Epidermal growth factor (EGFs), Fibroblast growth factor (FGFs), Endothelial cell growth factor (ECGF), Insulin-like growth factor 1 (IGF-1), Platelet-derived growth factor (PDGF), Nerve growth factor (NGF), and any combination thereof.

The hydrogels described herein provide a vehicle for stem cells that can beneficially deliver the stem cells to the site that is needed in a subject without damage to the cells or the tissue to be treated.

According to some embodiments, the solubility of the hydrogel is sufficiently high that it will completely degrade in less than 4 weeks after incorporation into the internal body cavity. According to certain embodiments, the solubility of the hydrogel is sufficiently high that it will completely degrade in less than 2 weeks after incorporation into the internal body cavity. According to additional embodiments, the solubility of the hydrogel is sufficiently high that it will completely degrade in less than 1 week, 4 days, 2 days, or 1 day after incorporation into the internal body cavity.

It is further envisaged that the hydrogels described herein can be used as a microenvironment for supporting membrane enveloped bodies such as eukaryotic cells, unicellular organisms, viruses and cellular organelles. The hydrogels described herein allow for maintaining the membrane enveloped bodies intact. The hydrogel may further comprise agents that support the viability and/or activity of said membrane enveloped bodies. The hydrogel may further comprise agents controlling the smoothness and the adhesion of the patch created. As a non-limiting example, the gel may contain hyaluronic acid.

The term "membrane" as used herein refers to a biological membrane that consists of a double layer of lipids and proteins that surrounds or envelops cells and organelles.

According to an additional aspect, the present invention provides a pharmaceutical composition comprising eukaryotic cells, unicellular organisms, viruses and/or cellular organelles embedded in a biodegradable thermoreversible hydrogel according to the invention.

According to some embodiments, the unicellular organisms are selected from the group consisting of archaea and bacteria.

According to some embodiments, the eukaryotic cells are animal or human cells.

According to some embodiments, the organelles are selected from the group consisting of nuclei, mitochondria, and chloroplasts.

The membrane enveloped bodies described herein may serve as a platform for heterologous gene expression. According to some embodiments, the membrane enveloped bodies described herein are modified to over express a heterologous gene. According to other embodiments, the membrane enveloped bodies described herein are modified to express a recombinant antibody.

According to some embodiments, the membrane enveloped bodies serve as genetic modifying factor carriers. The term "genetic modifying factor" as used herein refers to a compound that affects the expression of genes in host cells.

EXAMPLES

Example 1—Evaluation of Stem Cells Viability in a Thermoreversible Hydrogel

Hydrogels containing 27.0% Pluronic F-127 Ethylene Oxide/Propylene Oxide Block Copolymer, 1.0% Polyethylene glycol, average MW=400 (PEG-400), and 0.2% Hydroxypropylmethyl cellulose (HPMC); with the remainder water for injection (about 71.8%) are mixed with lineage specific precursor/progenitor (LSP) cells. The LSP cells are prepared according to a method described in U.S. Pat. No. 8,709,802. The concentration of the cells suspended in the hydrogel solution can mimic that of the tissue to be generated. The cell concentration is between 1000 and 10 million cells per mL. Cell viability in the hydrogel is evaluated by removing a slice of the hydrogel at predefined time intervals after mixing of said cells with the hydrogel, and using the slice to expand the cells in culture. Cell viability is measured by standard assays as known in the art.

Example 2—Preclinical Trials

Preclinical trials in rodent models for myocardial infarction are performed. Samples containing hydrogels embedding masenchymal cells at concentrations between $10^2$ to $10^7$ cells per mL are examined. The cell-laden hydrogel is administered to murine models of myocardial infarction. Murine model of myocardial infarction is prepared, for example, as described in Volk et al. (Volk et al., J Vis Exp. 2009; (32): 1438). The administration procedure is performed using a catheter as described in U.S. Pat. No. 8,079,982. The myocardial infarction area is monitored in the days after treatment as known in the art.

Example 3—Preclinical Trials

An animal study is performed according to a guidance published by The European Agency for the Evaluation of Medicinal Products Evaluation of Medicine for Human Use (ema.europa.eu/docs/en_GB/document_library/Scientific_guideline/2009/09/WC500003315.pdf).

The preclinical studies include evaluating a variety of parameters such as: determination of drug solubility, in vitro permeation studies, anti-inflammatory test, pyrogenicity tests, biodegradation rate, traces of cells within the tissue, in vivo cell penetration and targeting studies, and histological study.

The preclinical studies further include: scanning microscopic, pharmacodynamic studies, pharmacokinetic evaluation toxicity and safety studies, and irritation studies.

The clinical studies are conducted according to protocols approved by the Institutional Animal Ethical Committee (IAEC).

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A method for treating a cardiac disease or disorder in a subject in need thereof, the method comprises administering between the pericardium layer and the epicardium layer of said subject a pharmaceutical composition comprising stem cells and/or progenitor cells embedded in a biodegradable thermoreversible hydrogel, wherein the hydrogel is characterized by a viscosity of less than 200 Pa·s between 4° C. and 12° C., and a viscosity of more than 1,000 Pa·s at 37° C., and/or wherein said hydrogel comprises ethylene oxide/propylene oxide block copolymer, hydroxypropylmethylcellulose (HPMC) and an adhesive agent, wherein the composition is applied to form two different layers, each layer characterized by different mechanical properties and/or different diffusion coefficient and wherein one layer is towards the epicardium and characterized by a peak detachment force of at least 1.3 N, and the other, outer layer is towards the pericardium and characterized by a peak detachment force of less than 0.1 N.

2. The method of claim 1, wherein the hydrogel is characterized by flexibility sufficient to allow the tissue to which said composition is applied to move, contract, and/or expand with no significant loss of its original flexibility.

3. The method of claim 1, wherein the hydrogel is characterized by peel strength adhesiveness according to ASTM standard D2256-03 of 0.5-5.0 N cm$^{-2}$ at 37° C.

4. The method of claim 1, wherein the hydrogel comprises carboxymethyl cellulose (CMC).

5. The method of claim 1, wherein the stem cells are selected from the group consisting of embryonic stem cells (ESCs), induced pluripotent stem cells (iPSCs), myoblasts, bone marrow stem cells (BMSCs), mesenchymal stem cells, cardiac stem cells, and any combination thereof.

6. The method of claim 1, wherein the pharmaceutical composition comprises lineage specific precursor/progenitor (LSP) cells.

7. The method of claim 1, wherein the progenitor cells are of the mesodermal lineage.

8. The method of claim 1, wherein the hydrogel is characterized by a viscosity of more than $3 \times 10^3$ Pa·s at 37° C.

9. The method of claim 1, wherein the hydrogel is characterized by a peak detachment force of at least 0.001 N.

10. The method of claim 1, wherein the hydrogel comprises between 15% and 35% (w/w) ethylene oxide/propylene oxide block copolymer.

11. The method of claim 1, wherein the hydrogel comprises between 0.01% and 1% (w/w) hydroxypropylmethylcellulose (HPMC).

12. The method of claim 1, wherein the hydrogel comprises PEG.

13. The method of claim 1, wherein the hydrogel comprises between 20% and 30% (w/w) ethylene oxide/propylene oxide block copolymer; between 0.05% and 0.5% (w/w) hydroxypropylmethylcellulose (HPMC); between 0.1% and 2.5% (w/w) polyethylene glycol (PEG)-400; in addition to nutrients and isotonicity agents required for sustaining cell viability and the balance water.

14. The method of claim 1, wherein the hydrogel comprises between 20% and 30% (w/w) of an ethylene oxide/propylene oxide triblock copolymer characterized by an average molar mass of 13,000 and a general formula E106 P70 E106; between 0.05% and 0.3% HPMC; between 0.4% and 2.5% PEG-400; in addition to nutrients and isotonicity agents required for sustaining cell viability and the balance water.

15. The method of claim 1, wherein the hydrogel further comprises a component selected from the group consisting of adhesive and thickening compounds; bonding agents; pH-modifying substances; diffusion coatings; plasticizers; components for increasing permeability within the hydrogel; swellable excipients; matrix forming polymers; tight junction modifiers/cell membrane permeability enhancers; and any combination thereof.

16. The method of claim 1, wherein the cardiac disease or disorder is myocardial infarction or arrhythmia.

17. A method for accurate delivery of a pharmaceutical composition to a precise location beneath the pericardium without penetrating the cardiac muscle, the method comprising:
(i) mixing of stem cells and/or progenitor cells and the biodegradable thermoreversible hydrogel according to claim 1;
(ii) inflating a balloon to open a cavity between the myocardium and the pericardium, and adjacent to the presumptive scar tissue localization;
(iii) identifying the heart scar tissue localization; and
(iv) releasing the mixture of step (i) into the scar tissue localization identified in step (iii), wherein the mixture is applied to form two different layers, each having different mechanical properties and/or different diffusion coefficients, and wherein one layer is towards the myocardium and characterized by a peak detachment force of at least 1.3 N, and the other, outer layer is towards the pericardium characterized by a peak detachment force of less than 0.1 N.

18. The method of claim 17, wherein step (iii) comprising detecting ECG signal levels for identifying the heart scar tissue localization.

* * * * *